United States Patent
Lu et al.

(10) Patent No.: US 10,372,532 B2
(45) Date of Patent: Aug. 6, 2019

(54) MEMORY ARRAY AND MEASURING AND TESTING METHODS FOR INTER-HAMMING DIFFERENCES OF MEMORY ARRAY

(71) Applicant: Taiwan Semiconductor Manufacturing Co., Ltd., Hsinchu (TW)

(72) Inventors: Shih-Lien Linus Lu, Hsinchu (TW); Kun-Hsi Li, Hsinchu (TW); Saman M. I. Adham, Kanata (CA)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 167 days.

(21) Appl. No.: 15/677,414

(22) Filed: Aug. 15, 2017

(65) Prior Publication Data

US 2018/0157555 A1    Jun. 7, 2018

Related U.S. Application Data

(60) Provisional application No. 62/430,967, filed on Dec. 7, 2016.

(51) Int. Cl.
*H03M 13/15* (2006.01)
*G06F 11/10* (2006.01)
*H03M 13/19* (2006.01)
(Continued)

(52) U.S. Cl.
CPC ... *G06F 11/1048* (2013.01); *G01N 35/00594* (2013.01); *G01N 35/00732* (2013.01);
(Continued)

(58) Field of Classification Search
CPC .............. G06F 11/1048; G06F 11/073; G01N 35/00594; G01N 35/00732;
(Continued)

(56) References Cited

U.S. PATENT DOCUMENTS 6,215,898 B1 * 4/2001 Woodfill .................. G06K 9/32
382/154
6,557,080 B1 * 4/2003 Burger ................ G06F 12/0862
711/137

(Continued)

OTHER PUBLICATIONS

Yao et al., ClockPUF: Physical Unclonable Functions based on Clock Networks, 2013, EDAA, pp. 1-6. (Year: 2013).*
Hiller, Key Derivation with Physical Unclonable Functions, Jul. 11, 2016, Technische Universitat Munchen, pp. 1-153. (Year: 2016).*

*Primary Examiner* — John J Tabone, Jr.
(74) *Attorney, Agent, or Firm* — McClure, Qualey & Rodack, LLP

(57) ABSTRACT

A memory device is provided. The memory device includes a memory array including a plurality of sections, and an inter-hamming difference analyzer. Each section includes a plurality of bits, and the numbers of the bits of the plurality of sections are the same. The inter-hamming difference analyzer is configured to obtain contents of the plurality of sections operating in different operating conditions, to obtain a plurality of inter-hamming differences of the contents, and to provide a maximum inter-hamming difference and a minimum inter-hamming difference among the inter-hamming differences of the plurality of sections. The inter-hamming difference represents the number of unlike bits between the content of one section corresponding to a first operating condition and the content of another section corresponding to a second operating condition that is different from the first operating condition.

20 Claims, 10 Drawing Sheets

(51) Int. Cl.
*G01N 35/00* (2006.01)
*G06F 11/07* (2006.01)
*G11C 29/50* (2006.01)

(52) U.S. Cl.
CPC ........... *G06F 11/073* (2013.01); *G11C 29/50* (2013.01); *H03M 13/1575* (2013.01); *H03M 13/19* (2013.01); *G01N 2035/00782* (2013.01); *G11C 2029/5002* (2013.01)

(58) Field of Classification Search
CPC .......... G01N 2035/00782; G11C 29/50; G11C 2029/5002; H03M 13/19; H03M 13/1575
USPC ................................. 714/777, 763, 768, 773
See application file for complete search history.

(56) References Cited

U.S. PATENT DOCUMENTS

| | | | |
|---|---|---|---|
| 8,112,700 B2 * | 2/2012 | Kuekes | B82Y 10/00 708/1 |
| 9,503,169 B1 * | 11/2016 | Lee | H04L 1/0618 |
| 2006/0176167 A1 * | 8/2006 | Dohrmann | G08B 25/001 340/506 |
| 2013/0262962 A1 | 10/2013 | Chen et al. | |
| 2014/0241086 A1 | 8/2014 | O'Connell | |
| 2017/0099066 A1 * | 4/2017 | Noh | H03M 13/136 |
| 2017/0126360 A1 * | 5/2017 | Millar | H04L 1/0045 |
| 2018/0069628 A1 * | 3/2018 | Wei | H04B 10/524 |

* cited by examiner

Cond_1

|       | Content |
|-------|---------|
| 410A → SEC_1 | 0101 |
| 410B → SEC_2 | 0101 |
| 410C → SEC_3 | 0101 |
| 410D → SEC_4 | 0101 |

Cond_2

|       | Content |
|-------|---------|
| 420A → SEC_1 | 0100 |
| 420B → SEC_2 | 0101 |
| 420C → SEC_3 | 0101 |
| 420D → SEC_4 | 0101 |

|  | Content |
|---|---|
| SEC_1 | 1000 |
| SEC_2 | 1000 |
| SEC_3 | 0110 |
| SEC_4 | 0110 |

Cond_3

430A → SEC_1
430B → SEC_2
430C → SEC_3
430D → SEC_4

| 420A | Cond_2 | Cond_1 | XOR_SECTION | Inter_HD |
|---|---|---|---|---|
| | 0100 | 0101 | NA | NA |
| | 0101 | 0101 | 0001 | 1 |
| | 0101 | 0101 | 0001 | 1 |
| | 0101 | 0101 | 0001 | 1 |

FIG. 5A

| 420B | Cond_2 | Cond_1 | XOR_SECTION | Inter_HD |
|---|---|---|---|---|
| | 0100 | 0101 | 0000 | 0 |
| | 0101 | 0101 | NA | NA |
| | 0101 | 0101 | 0000 | 0 |
| | 0101 | 0101 | 0000 | 0 |

FIG. 5B

|  | Cond_2 | Cond_1 | XOR_SECTION | Inter_HD |
|---|---|---|---|---|
| | 0100 | 0101 | 0000 | 0 |
| | 0101 | 0101 | 0000 | 0 |
| 420C → | 0101 | 0101 | NA | NA |
| | 0101 | 0101 | 0000 | 0 |

FIG. 5C

|  | Cond_2 | Cond_1 | XOR_SECTION | Inter_HD |
|---|---|---|---|---|
| | 0100 | 0101 | 0000 | 0 |
| | 0101 | 0101 | 0000 | 0 |
| | 0101 | 0101 | 0000 | 0 |
| 420D → | 0101 | 0101 | NA | NA |

FIG. 5D

|  | 430A | 410B | 410A | | |
|--|------|------|------|--|--|
|  |  | Cond_3 | Cond_1 | XOR_SECTION | Inter_HD |
|  |  | 1000 | 0101 | NA | NA |
|  |  | 1000 | 0101 | 1101 | 3 |
|  |  | 0110 | 0101 | 1101 | 3 |
|  |  | 0110 | 0101 | 1101 | 3 |

| 430B | Cond_3 | Cond_1 | XOR_SECTION | Inter_HD |
|------|--------|--------|-------------|----------|
|      | 1000   | 0101 | 1101      | 3        |
|      | 1000 | 0101 | NA          | NA       |
|      | 0110   | 0101   | 1101        | 3        |
|      | 0110   | 0101   | 1101        | 3        |

|         | 410B     | 410A    |             |          |
|---------|----------|---------|-------------|----------|
|         | Cond_3   | Cond_1  | XOR_SECTION | Inter_HD |
| 430C    | ~~1000~~ | 0101    | 0011        | 2        |
|         | ~~1000~~ | 0101    | 0011        | 2        |
|         | 0110     | ~~0101~~| NA          | NA       |
|         | ~~0110~~ | 0101    | 0011        | 2        |

|         | 410B     | 410A    |             |          |
|---------|----------|---------|-------------|----------|
|         | Cond_3   | Cond_1  | XOR_SECTION | Inter_HD |
|         | ~~1000~~ | 0101    | 0011        | 2        |
| 430D    | ~~1000~~ | 0101    | 0011        | 2        |
|         | ~~0110~~ | 0101    | 0011        | 2        |
|         | 0110     | ~~0101~~| NA          | NA       |

MEMORY ARRAY AND MEASURING AND TESTING METHODS FOR INTER-HAMMING DIFFERENCES OF MEMORY ARRAY

CROSS REFERENCE TO RELATED APPLICATIONS

This application claims priority of U.S. Provisional Application No. 62/430,967, filed on Dec. 7, 2016, the entirety of which is incorporated by reference herein.

BACKGROUND

Although they are manufactured in large numbers, each integrated circuit (IC) is unique due to physical randomness, even when the same manufacturing process and the same material are used. The inherent variations can be extracted and used as its unique identification, such as DNA or fingerprints with human beings. Recently, security researchers have proposed different ways to take advantage of physical randomness to build physically unclonable functions (PUFs). One type of PUF is built with an SRAM memory array. A way to build a PUF using SRAM is based on the power-up states of the memory cells in an SRAM.

BRIEF DESCRIPTION OF THE DRAWINGS

Aspects of the present disclosure are best understood from the following detailed description when read with the accompanying figures. It should be noted that, in accordance with the standard practice in the industry, various nodes are not drawn to scale. In fact, the dimensions of the various nodes may be arbitrarily increased or reduced for clarity of discussion.

FIG. 4A shows the exemplary response of the PUFs of a memory array under the first operating condition Cond_1.

FIG. 4B shows the exemplary response of the PUFs of a memory array under the second operating condition Cond_2.

FIG. 4C shows the exemplary response of the PUFs of a memory array under the third operating condition Cond_3.

FIG. 5A shows the table illustrating the Inter-HDs of the contents between the sections 410B through 410D of FIG. 4A and the section 420A of FIG. 4B.

FIG. 5B shows the table illustrating the Inter-HDs of the contents between the sections 410A, 410C and 410D of FIG. 4A and the section 420B of FIG. 4B.

FIG. 5C shows the table illustrating the Inter-HDs of the contents between the sections 410A, 410B and 410D of FIG. 4A and the section 420C of FIG. 4B.

FIG. 5D shows the table illustrating the Inter-HDs of the contents between the sections 410A through 410C of FIG. 4A and the section 420D of FIG. 4B.

FIG. 6A shows the table illustrating the Inter-HDs of the contents between the sections 410B through 410D of FIG. 4A and the section 430A of FIG. 4C.

FIG. 6B shows the table illustrating the Inter-HDs of the contents between the sections 410A, 410C and 410D of FIG. 4A and the section 430B of FIG. 4C.

FIG. 6C shows the table illustrating the Inter-HDs of the contents between the sections 410A, 410B and 410D of FIG. 4A and the section 430C of FIG. 4C.

FIG. 6D shows the table illustrating the Inter-HDs of the contents between the sections 410A through 410C of FIG. 4A and the section 430D of FIG. 4C.

DETAILED DESCRIPTION

Figure 1:
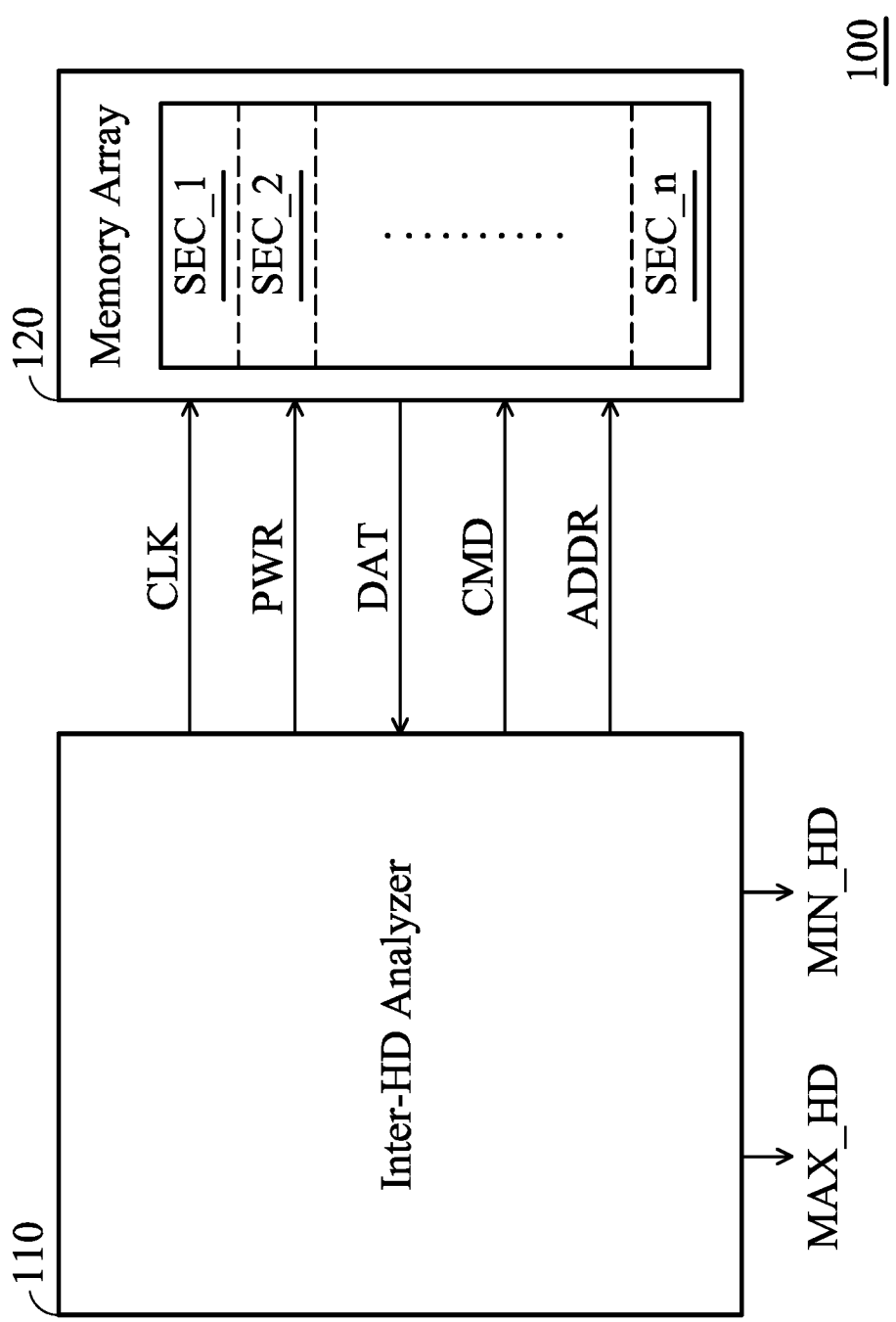
FIG. 1 shows a memory device, in accordance with some embodiments of the disclosure.

The following disclosure provides many different embodiments, or examples, for implementing different nodes of the subject matter provided. Specific examples of components and arrangements are described below to simplify the present disclosure. These are, of course, merely examples and are not intended to be limiting. In some embodiments, the formation of a first node over or on a second node in the description that follows may include embodiments in which the first and second nodes are formed in direct contact, and may also include embodiments in which additional nodes may be formed between the first and second nodes, such that the first and second nodes may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Some variations of various embodiments are described. Throughout the various views and illustrative embodiments, like reference numbers are used to designate like elements. It should be understood that additional operations can be provided before, during, and/or after a disclosed method, and some of the operations described can be replaced or eliminated for other embodiments of the method.

A physical "function" called Physically Unclonable Function (PUF) is used as a security feature for integrated circuits (ICs) or chips. A PUF in cryptography is a physical object which is easy to evaluate and produce an output but the output is very hard to predict. A PUF can be used as a unique identification or key in secure computing and communication where a challenge is given to the PUF and a response is demanded. If the response matches the pre-agreed response then the PUF is verified as the authentic IC or chip.

A PUF should have the following properties: uniqueness (e.g., individualism), being inherent (e.g., born with), being unclonable (e.g., cannot be mimicked or duplicated), and being repeatable (e.g., reliable).

Regarding uniqueness, each PUF is distinctive and different from all other PUFs on the same chip or on other chips.

Regarding inherence, each PUF generates its unique output based on intrinsic properties of the PUF.

Regarding being unclonable, it is impossible to make an exact replica even when the exact manufacturing process is used.

Regarding repeatability, the response (or an output) of a PUF should not be affected by the environment and age.

One of the properties, "uniqueness," can be defined and measured by Hamming distances/differences (HDs). There are two types of HDs for a PUF: Intra-Hamming distance/difference (Intra-HD) and Inter-Hamming distance/difference (Inter-HD).

Intra-HD represents the difference between two responses when the same challenge is applied twice to the same PUF, i.e. Intra-HD is the HD between the same PUF operating at separate times. The Intra-HD metric may measure the HD between multiple reads of PUF bits on a single integrated circuit. The Intra-HD may help to quantify the reliability of the PUF and the error rate of the bits of PUF. An Intra-HD of 0 indicates that the PUF is perfectly repeatable.

Inter-HD is the HD between different PUFs. Inter-HD assesses the uniqueness of PUF and generally should be reasonably close to half of the PUF length. For example, Inter-HD of responses from different PUFs should be as close to 50% as possible since a PUF's response is random with 50% 0s and 50% 1s in binary. If the Inter-HD of all responses of PUFs is 50% then each PUF will have a different signature, and each is unique. There are different ways to build a PUF. Memory-based PUFs are recognized as being very efficient and having a low cost. Among the types of memory-based PUFs, SRAM-based PUFs are very popular. An important characterization task is to verify that PUFs made with memory (such as SRAM) have an Inter-HD as close to 50% as possible.

FIG. 1 shows a memory device 100, in accordance with some embodiments of the disclosure. The memory device 100 includes an inter-hamming distance/difference (Inter-HD) analyzer 110 and a memory array 120. The memory array 120 is formed by multiple memory cells arranged in an array, and the memory cells are divided into multiple sections SEC_1 through SEC_n. In some embodiments, the sections SEC_1 through SEC_n have individual locations within the memory array 120. Furthermore, the number of memory cells in each of the sections, SEC_1 through SEC_n, is the same. For example, the number of memory cells in section SEC_1 is identical to the number of memory cells in section SEC_2.

The Inter-HD analyzer 110 is capable of measuring the Inter-HDs of the sections SEC_1 through SEC_n of the memory array 120, and the contents of the sections SEC_1 through SEC_n include a response of a PUF under an operating condition. In information theory, the Inter-HD between the contents of two sections with an equal number of characters is the number of positions at which the corresponding characters of the two contents are different. Furthermore, Inter-HD represents the number of characters that are to be replaced in order to match the two contents exactly. The content of each section includes a binary string, which is a string with binary characters 0 and 1. Inter-HD between two binary strings (or vectors) is the number of bits that are different between the two binary strings.

In some embodiments, the Inter-HD analyzer 110 provides a power supply PWR and an operation clock CLK to power on the memory array 120. In some embodiments, the power supply PWR and the operation clock CLK are control signals capable of controlling the characteristics of the power supply and clock for the memory array 120. When the memory array 120 is powered on (e.g., in a power-up state), the Inter-HD analyzer 110 provides a command signal CMD and an address signal ADDR to the memory array 120 via the corresponding buses, so as to read data DAT from the memory array 120. The data DAT includes the contents of one or more sections in the memory array 120. Moreover, the read section has a location that corresponds to the address signal ADDR.

In response to the command signal CMD and the address signal ADDR, the memory array 120 can provide the response of the PUF under an operating condition corresponding to a voltage level of the power supply PWR and a frequency value of the operation clock CLK from the Inter-HD analyzer 110.

By providing variable voltage level of the power supply PWR and variable frequency value of the operation clock CLK, the Inter-HD analyzer 110 can obtain the contents of various responses of the PUF under different operating conditions. According to the contents of various responses of the PUF, the Inter-HD analyzer 110 determines the Inter-HDs between the responses to provide a maximum Inter-HD MAX_HD and a minimum Inter-HD MIN_HD for the memory array 120.

Figure 2:
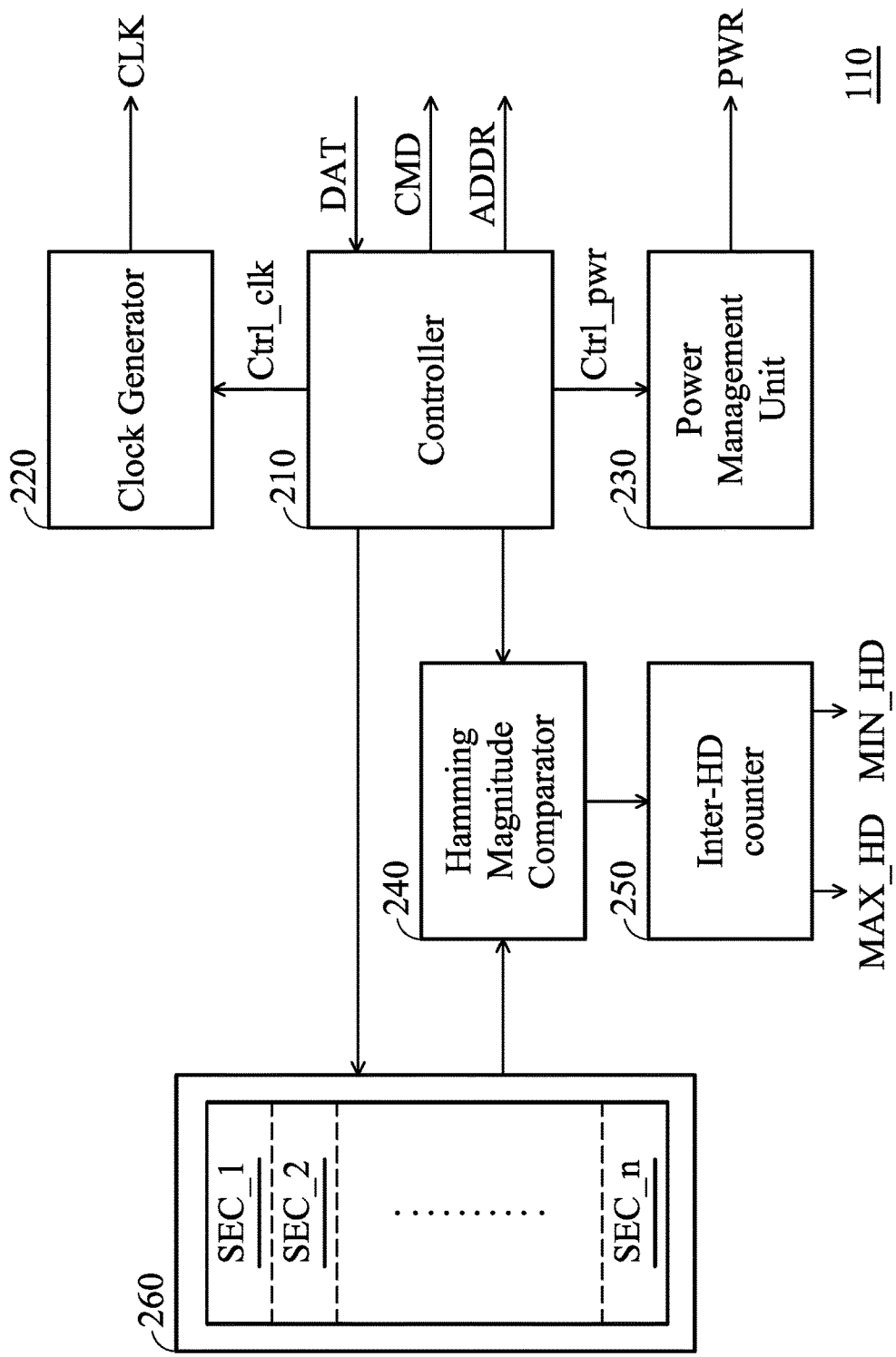
FIG. 2 shows an exemplified diagram illustrating the Inter-HD analyzer of FIG. 1, in accordance with some embodiments of the disclosure.

FIG. 2 shows an exemplified diagram illustrating the Inter-HD analyzer 110 of FIG. 1, in accordance with some embodiments of the disclosure. In some embodiments, the Inter-HD analyzer 110 and the memory array 120 are implemented in an IC.

Referring to FIG. 1 and FIG. 2 together, the Inter-HD analyzer 110 includes a controller 210, a clock generator 220, a power management unit 230, a hamming magnitude comparator 240, a Inter-HD counter 250, and a storage device 260.

The clock generator 220 is coupled to the controller 210. The controller 210 is capable of providing a control signal Ctrl_clk to the clock generator 220, so as to provide the operation clock CLK to the memory array 120 and to control the characteristics of the operation clock CLK. For example, in response to the control signal Ctrl_clk, the characteristics of the operation clock CLK, such as frequency, duty cycle, slew rate, and so on, are controlled or changed. The operating condition of the memory array 120 is determined according to the characteristics of the operation clock CLK.

The power management unit 230 is coupled to the controller 210. The controller 210 is capable of providing a control signal Ctrl_pwr to the power management unit 230, so as to provide the power supply PWR to the memory array 120 and to control the characteristics of the power supply PWR. For example, in response to the control signal Ctrl_pwr, the characteristics of the power supply PWR, such as voltage level, are controlled or changed. Furthermore, the operating condition of the memory array 120 is determined according to the changed characteristics of the power supply PWR.

In some embodiments, the operation clock CLK and the power supply PWR are provided by other circuits that are separated from the Inter-HD analyzer 110. Similarly, the Inter-HD analyzer 110 can provide the control signals Ctrl_clk and Ctrl_pwr to the circuits, so as to control the characteristics of the operation clock CLK and the power supply PWR to be provided to the memory array 120.

When the power supply PWR with a first voltage level V1 (not shown) and/or the operation clock CLK with a first frequency value F1 (not shown) are provided to the memory array 120, the memory array 120 is powered on under a first operating condition Cond_1, and the response of the PUF corresponding to the first operating condition Cond_1 is obtained based on the power-up states of the memory cells of the memory array 120. Next, the Inter-HD analyzer 110 provides the address signal ADDR corresponding to the sections SEC_1 through SEC_n and the command signal CMD to the memory array 120, so as to read the data DAT regarding the response of the PUF corresponding to the first operating condition Cond_1, i.e. the contents of the sections SEC_1 through SEC_n in sequence. After obtaining the contents of the sections SEC_1 through SEC_n, the controller 210 stores the contents of the sections SEC_1 through SEC_n into the storage device 260.

The storage device 260 is a memory array, which is used to store or copy the response of the PUF under the first operating condition Cond_1. In some embodiments, the storage device 260 is used to store an initial response of the PUF corresponding to an initial operating condition. In some embodiments, the storage device 260 is formed by multiple memory cells, and the memory cells are also divided into multiple sections SEC_1 through SEC_n. In some embodiments, the storage device 260 has the same capacity as the memory array 120. Furthermore, the contents of the sections SEC_1 through SEC_n from the memory array 120 are stored into the corresponding sections SEC_1 through SEC_n in the storage device 260, respectively. For example, the content of the section SEC_1 from the memory array 120 is stored into the section SEC_1 of the storage device 260, the content of the section SEC_2 from the memory array 120 is stored into the section SEC_2 of the storage device 260, and so on.

After the contents of the sections SEC_1 through SEC_n corresponding to the first operating condition Cond_1 are stored in the storage device 260, the controller 210 provides the control signals Ctrl_clk and Ctrl_pwr to the clock generator 220 and the power management unit 230, so as to provide the power supply PWR with a second voltage level V2 (not shown) and/or the operation clock CLK with a second frequency value F2 (not shown) to power up the memory array 120 under a second operating condition Cond_2. Similarly, when the memory array 120 is powered on in the second operating condition Cond_2, and the response of the PUF corresponding to the second operating condition Cond_2 is obtained based on the power-up states of the memory cells in the memory array 120. Next, the Inter-HD analyzer 110 provides the address signal ADDR corresponding to the sections SEC_1 through SEC_n and the command signal CMD to the memory array 120, so as to read the data DAT regarding the contents of the sections SEC_1 through SEC_n under the second operating condition Cond_2 in sequence.

After the sections SEC_1 through SEC_n from the memory array 120 are received, the Inter-HDs between the sections corresponding to the second operating condition Cond_2 (i.e., the sections from the memory array 120) and the sections corresponding to the first operating condition Cond_1 (i.e., the sections stored in the storage device 260) are obtained by the hamming magnitude comparator 240. As described above, the sections from the memory array 120 include the response of the PUF under the second operating condition Cond_2, and the sections stored in the storage device 260 include the response of the PUF under the first operating condition Cond_1. Next, the Inter-HD counter 250 finds the highest value among all of the Inter-HDs as the maximum Inter-HD MAX_HD, and finds the lowest value among all of the Inter-HDs as the minimum Inter-HD MIN_HD for the memory array 120. The operation of the hamming magnitude comparator 240 and the Inter-HD counter 250 will be described in detail below.

Figure 3:
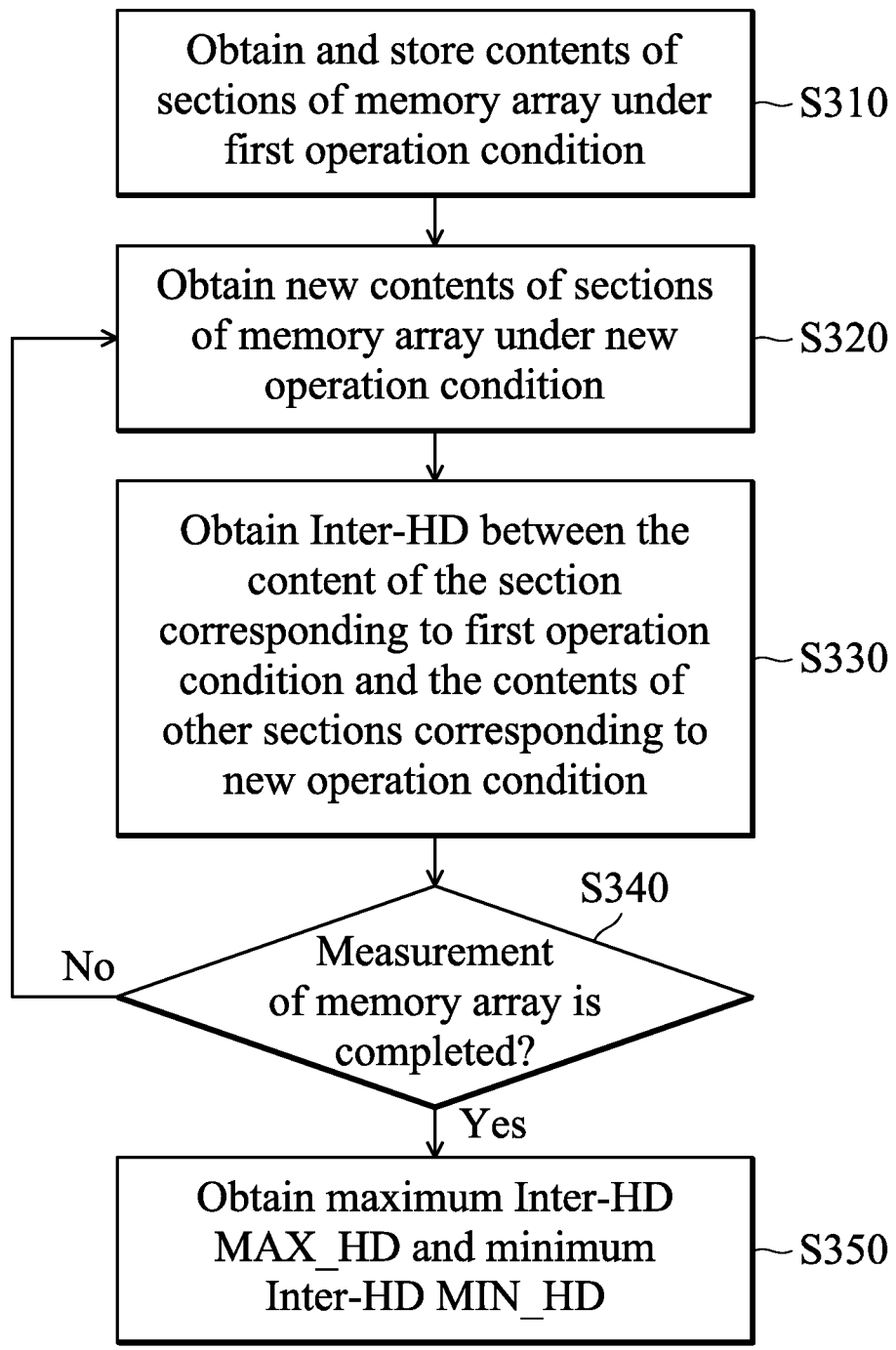
FIG. 3 shows a method for measuring Inter-HDs of a memory array, in accordance with some embodiments of the disclosure.

FIG. 3 shows a method for measuring Inter-HDs of a memory array 120 of FIG. 1, in accordance with some embodiments of the disclosure. In some embodiments, the method of FIG. 3 is performed by the Inter-HD analyzer 110 of FIG. 1. The memory array 120 is formed by multiple memory cells, and the memory cells are divided into multiple sections SEC_1 through SEC_n. Each of the sections SEC_1 through SEC_n has its individual location in the memory array 120. Furthermore, the sizes of the sections SEC_1 through SEC_n are the same. The method of FIG. 3 is capable of measuring Inter-HDs of various types of memory arrays. Furthermore, some operations described in FIG. 3 can be replaced, eliminated, or moved around for additional embodiments of the method, and additional operations can be provided before, during, and after the method.

In operation S310, the memory array 120 is powered on under a first operating condition Cond_1, and multiple contents of the sections SEC_1 through SEC_n corresponding to the first operating condition Cond_1 are obtained. As described above, the contents of the sections SEC_1 through SEC_n including the response of the PUF under the first operating condition Cond_1 are obtained based on the power-up states of the memory cells in the memory array 120. Furthermore, the contents of the sections SEC_1 through SEC_n corresponding to the first operating condition Cond_1 are stored in a memory array, such as the storage device 260 of FIG. 2. In some embodiments, the first operating condition Cond_1 is an initial operating condition for measuring the memory array 120. In the first operating condition Cond_1, the power supply PWR with a first voltage level V1, and/or the operation clock CLK with a first frequency value F1 are applied to the memory array 120.

In operation S320, the memory array 120 is powered on under a new operating condition (e.g., the second operating condition Cond_2) that is different from the first operating condition Cond_1, and the new contents of the sections SEC_1 through SEC_n including the response of the PUF under the new operating condition are obtained. The characteristics of the power supply PWR, and/or the operation clock CLK of the new operating condition are different from that of the first operating condition Cond_1.

In operation S330, the Inter-HDs between the content of the section having a location under the first operating condition Cond_1 and the contents of the other sections having other locations under the new operating condition are determined, measured or obtained. An example illustrating how to determine the Inter-HDs is presented in FIGS. 4A-6D. In some embodiments, the Inter-HDs are determined by the hamming magnitude comparator 240 of FIG. 2. Furthermore, no Inter-HD between the content of the section having a location under the first operating condition Cond_1 and the content of the section having the same location under the new operating condition is determined. If the number of sections SEC_1 through SEC_n of the memory array 120 is N, the number of Inter-HDs obtained in operation S330 is N×(N−1). The number of HDs will be described further below.

In operation S340, it is determined whether measurement of the Inter-HDs in the memory array 120 is completed. If the measurement of the memory array 120 has not been completed, the operations S320 and S330 are performed again. Thus, the memory array 120 is powered on under a new operating condition that is different from the previous operating conditions, and the new contents of the sections SEC_1 through SEC_n including the response of the PUF under the new operating condition are obtained. Furthermore, the Inter-HDs between the content of the section having a location under the first operating condition Cond_1 and the contents of the other sections having other locations under the new operating condition are determined.

If the measurement of the memory array 120 has completed, a maximum Inter-HD MAX_HD and a minimum Inter-HD MIN_HD among the whole HDs of the memory array 120 are obtained in operation S350. Thus, an Inter-HD range of the memory array 120 is obtained according to the maximum Inter-HD MAX_HD and the minimum Inter-HD MIN_HD. In some embodiments, the Inter-HD range does not overlap the Intra-HD range for the memory array 120. In some embodiments, the Intra-HD range of the memory array 120 is obtained in advance. If it is determined that the Inter-HD range does not overlay the Intra-HD range, verification of the memory array 120 is successful and it is determined that PUFs of the memory array 120 are hard to predict, e.g., the PUFs are sufficient for the security feature of the memory array 120. Conversely, if the Inter-HD range overlays the Intra-HD range, the verification of the memory array 120 is unsuccessful and it is determined that PUFs of the memory array 120 are easy to predict, e.g., the PUFs are insufficient for the security feature of the memory array 120.

In some embodiments, the method of FIG. 3 is performed by an Inter-HD analyzer 110 of FIG. 2, a controller, a microcontroller, a processor or a processing circuitry based on one or more microprocessors, microcontrollers, digital signal processors, programmable logic devices, etc. Furthermore, the memory array 120 to be measured, the Inter-HD analyzer 110, the controller or the microcontroller are implemented in an IC or a chip (or die). By measuring the IC with a test apparatus, the maximum Inter-HD MAX_HD, the minimum Inter-HD MIN_HD and the Inter-HD range are obtained in an on-line manner without loading the contents of all of the responses in an off-line manner, and a more detailed description is presented in FIG. 7.

FIGS. 4A-4C show exemplary responses of the PUFs under three operating conditions Cond_1 through Cond_3 for a memory array 120A, respectively. In order to simplify the description, the memory array 120A is a memory array capable of storing 16 bits of response, and the 16 bits of response is divided into 4 sections SEC_1 through SEC_4.

In some embodiments, the number of bits (k) in each section is equal to M/N (i.e., k=M/N), where M represents the total number of bits of the memory array, and N represents the number of sections in the memory array. For example, the number of bits in each of the sections SEC_1 through SEC_4 is equal to 4 (i.e., 16/4=4) in FIGS. 4A-4C.

FIG. 4A shows the exemplary response of the PUFs of the memory array 120A under the first operating condition Cond_1. In FIG. 4A, assuming that the response under the first operating condition Cond_1 is "0101010101010101", the contents of the sections SEC_1 through SEC_4 are "0101", "0101", "0101" and "0101", respectively. In order to simplify the description, the sections SEC_1 through SEC_4 under the first operating condition Cond_1 are named as the sections 410A through 410D, respectively.

FIG. 4B shows the exemplary response of the PUFs of the memory array 120A under the second operating condition Cond_2. In FIG. 4B, assuming that the response under the second operating condition Cond_2 is "0100010101010101", the contents of the sections SEC_1 through SEC_4 are "0100", "0101", "0101" and "0101", respectively. In order to simplify the description, the sections SEC_1 through SEC_4 under the second operating condition Cond_2 are named as the sections 420A through 420D, respectively.

FIG. 4C shows the exemplary response of the PUFs of the memory array 120A under the third operating condition Cond_3. In FIG. 4C, assuming that the response under the third operating condition Cond_3 is "1000100001100110", the contents of the sections SEC_1 through SEC_4 are "1000", "1000", "0110" and "0110", respectively. In order to simplify the description, the sections SEC_1 through SEC_4 under the third operating condition Cond_3 are named as the sections 430A through 430D, respectively.

The Inter-HDs among the 4 sections SEC_1 through SEC_4 are the number of bits differences between the 4 sections SEC_1 through SEC_4 under the operating conditions Cond_1 through Cond_3. For the contents of two different sections under the different operating conditions, the Inter-HD represents the number of unlike bits in the contents of the two different sections. For example, taking the section 410A of FIG. 4A and the section 420B of FIG. 4B as an example, the content "0101" of the section 410A is identical to the content "0101" of the section 420B, and the Inter-HD between the sections 410A and 420B is equal to zero. Furthermore, taking the section 420A of FIG. 4B and the section 430C of FIG. 4C as an example, the content "0100" of the section 420A is different from the content "0110" of the section 430C, and the Inter-HD is equal to one due to the bit closest to least significant bit (LSB) is different for the sections 420A and 430C.

FIGS. 5A-5D show tables illustrating the Inter-HDs of the contents between the sections SEC_1 through SEC_4 of the first operating condition Cond_1 of FIG. 4A and the second operating condition Cond_2 of FIG. 4B.

FIG. 5A shows the table illustrating the Inter-HDs of the contents between the sections 410B through 410D of FIG. 4A and the section 420A of FIG. 4B.

Referring to FIG. 2 and FIG. 5A together, assuming that the contents of the sections 410A through 410D (e.g., the sections SEC_1 through SEC_4 under the first operating conditions Cond_1) in FIG. 4A have been previously stored in the storage device 260 of FIG. 2. When obtaining the content of one section from the memory array 120A under the second operating conditions Cond_2, the Inter-HD analyzer 110 can determine the Inter-HD between the content of the one section from the memory array 120A and the contents of other sections stored in the storage device 260. For example, when obtaining the content "0100" of the section 420A (e.g., the section SEC_1 under the second operation condition Cond_2 of FIG. 4B) from the memory array 120A, the controller 210 provides the content "0100" of the section 420A to the hamming magnitude comparator 240. Furthermore, the controller 210 controls the storage device 260 to provide the contents "0101" of the sections 410B through 410D stored in the storage device 260 to the hamming magnitude comparator 240 except the content "0101" of the section 410A.

As described above, the hamming magnitude comparator 240 is a device for determining the Inter-HD between the contents of two different sections under the different operating conditions, and the two sections have different locations in the memory array. The Inter-HD represents the number of unlike bits in the contents of the two sections. In some embodiments, the Hamming magnitude comparator 240 performs a bitwise XOR operation of bits in the contents of the two sections, so as to obtain the Inter-HD between the two sections. For example, the Hamming magnitude comparator 240 performs a bitwise XOR operation of bits between the content "0100" of the section 420A and the contents '0101" of the sections 410B through 410D, so as to obtain intermediate results XOR_SECTION between the section 420A and the sections 410B through 410D.

In FIG. 5A, since the content "0100" of the section 420A is different from the contents "0101" of the section 410B, the intermediate results XOR_SECTION determined by the Hamming magnitude comparator 240 are "0001" (i.e., the least significant bits (LSBs) of "0100" and "0101" are different), and the Inter-HDs between the section 420A and the section 410B is 1. Similarly, the content "0101" of the section 410B is identical to the contents "0101" of the sections 410C and 410D, the intermediate results XOR_SECTION determined by the Hamming magnitude comparator 240 are "0001", and the Inter-HDs between the section 420A and the sections 410C and 410D are also 1. Furthermore, the Inter-HD between the section 420A and the section 410A (e.g., the section SEC_1 under the first operating condition Cond_1 of FIG. 4A) will not be calculated by the Hamming magnitude comparator 240 because the sections 410A and 420A are the sections having the same location under the different operating conditions Cond_1 and Cond_2. Specifically, the Inter-HD between the sections SEC_1 (e.g. 420A and 410A) having the same location under the different operating conditions is not available (NA). Furthermore, the number of Inter-HDs corresponding to the section 420A is equal to the number of sections SEC_1 through SEC_4 of the memory array 120A minus one. For example, the number of sections of the memory array 120A is 4, and the number of Inter-HDs corresponding to the section 420A is 3 (i.e., 4−1=3), such as the Inter-HD "1" between the sections 420A and 410B, the Inter-HD "1" between the sections 420A and 410C, and the Inter-HD "1" between the sections 420A and 410D.

FIG. 5B shows the table illustrating the Inter-HDs of the contents between the sections 410A, 410C and 410D of FIG. 4A and the section 420B of FIG. 4B.

In FIG. 5B, since the content "0101" of the section 420B is identical to the contents "0101" of the sections 410A, 410C and 410D, the intermediate results XOR_SECTION determined by the Hamming magnitude comparator 240 are "0000", and the Inter-HDs between the section 420B and the sections 410A, 410C and 410D are zero. Furthermore, the Inter-HD between the section 420B and the section 410B will not be calculated by the Hamming magnitude comparator 240 because the sections 410B and 420B are the sections having the same location under the different operating conditions Cond_1 and Cond_2. Specifically, the Inter-HD between the sections SEC_2 having the same location under the different operating conditions is not available (NA). Similarly, the number of Inter-HDs corresponding to the section 420B is 3, such as the Inter-HD "0" between the sections 420B and 410A, the Inter-HD "0" between the sections 420B and 410C, and the Inter-HD "0" between the sections 420B and 410D.

FIG. 5C shows the table illustrating the Inter-HDs of the contents between the sections 410A, 410B and 410D of FIG. 4A and the section 420C of FIG. 4B. Similarly, the content "0101" of the section 420C is identical to the contents "0101" of the sections 410A, 410B and 410D, and the intermediate results XOR_SECTION determined by the Hamming magnitude comparator 240 are "0000", thus the Inter-HDs are zero in FIG. 5C.

FIG. 5D shows the table illustrating the Inter-HDs of the contents between the sections 410A through 410C of FIG. 4A and the section 420D of FIG. 4B. Similarly, the content "0101" of the section 420D is identical to the contents "0101" of the sections 410A through 410C, and the intermediate results XOR_SECTION determined by the Hamming magnitude comparator 240 are "0000", thus the Inter-HDs are zero in FIG. 5D.

In FIGS. 5A through 5D, since the number of sections SEC_1 through SEC_4 of the memory array 120A is 4, the number of Inter-HDs of the memory array 120A between the first operating conditions Cond_1 and the second operating conditions Cond_2 is equal to 12 (i.e., 4×(4−1)).

As described above, the Inter-HD counter 250 of FIG. 2 is capable of finding the largest value and the least value among the Inter-HDs between the sections SEC_1 through SEC_4 under the operating conditions Cond_1 and Cond_2, so as to provide the maximum Inter-HD MAX_HD and the minimum Inter-HD MIN_HD of the memory array 120A. According to the Inter-HDs "1" of FIG. 5A and the Inter-HDs "0" of FIGS. 5B through 5D, the maximum Inter-HD MAX_HD is "1" and the minimum Inter-HD MIN_HD is "0".

In some embodiments, the Inter-HD range of the memory array 120A is determined according to the maximum Inter-HD MAX_HD, the minimum Inter-HD MIN_HD, and the number of bits (e.g., k) in each section. For example, the Inter-HD range is set as (MIN_HD/k, MAX_HD/k). According to "1" of the maximum Inter-HD MAX_HD and "0" of the minimum Inter-HD MIN_HD in FIGS. 5A-5D, the Inter-HD range of the memory array 120A is (0/4, 1/4). Converted into percentage, the Inter-HD range of the memory array 120A is (0%, 25%). As described above, according to the Inter-HD range and Intra-HD range of the memory array 120A, it is determined whether the PUFs are sufficient for the security feature of the memory array 120A. In some embodiments, the Intra-HD range of the memory array 120A is obtained in advance.

FIGS. 6A-6D show tables illustrating the Inter-HDs of the contents between the sections SEC_1 through SEC_4 of the first operating condition Cond_1 of FIG. 4A and the third operating condition Cond_3 of FIG. 4C.

As described above, the contents of the sections 410A through 410D (e.g., the sections SEC_1 through SEC_4 under the first operating conditions Cond_1) in FIG. 4A has been previously stored in the storage device 260. The Hamming magnitude comparator 240 performs a bitwise XOR operation of bits between the sections under the third operating condition Cond_3 and the sections under the first operating condition Cond_1 except the sections having the same location, so as to obtain intermediate results XOR_SECTION between the sections under the third operating condition Cond_3 of FIG. 4C and the sections under the first operating condition Cond_1 of FIG. 4A.

FIG. 6A shows the table illustrating the Inter-HDs of the contents between the sections 410B through 410D of FIG. 4A and the section 430A of FIG. 4C.

Taking the table of FIG. 6A as an example, according to the content "1000" of the section 430A and the contents "0101" of the sections 410B through 410D, the intermediate results XOR_SECTION determined by the Hamming magnitude comparator 240 of FIG. 2 are "1101", and the Inter-HDs between the section 430A and the sections 410B through 410D are 3. Furthermore, the Inter-HD between the sections SEC_1 (e.g., 430A and 410A) having the same location under the different operating conditions is not available (NA). Next, the Inter-HD counter 250 of FIG. 2 is capable of finding the largest value and the least value among the Inter-HDs between the sections SEC_1 through SEC_4 under the first operating condition Cond_1 and the third operating condition Cond_3, so as to obtain the maximum Inter-HD MAX_HD and the minimum Inter-HD MIN_HD of the memory array 120A.

FIG. 6B shows the table illustrating the Inter-HDs of the contents between the sections 410A, 410C and 410D of FIG. 4A and the section 430B of FIG. 4C. Similarly, the content "0101" of the sections 410A, 410C and 410D are different from the content "1000" of the section 430B, the intermediate results XOR_SECTION determined by the Hamming magnitude comparator 240 are "1101", and the Inter-HDs are 3 in FIG. 6B.

FIG. 6C shows the table illustrating the Inter-HDs of the contents between the sections 410A, 410B and 410D of FIG. 4A and the section 430C of FIG. 4C. In FIG. 6C, according to the content "0110" of the section 430C and the contents "0101" of the sections 410A, 410B and 410D, the intermediate results XOR_SECTION determined by the Hamming magnitude comparator 240 of FIG. 2 are "0011", and the Inter-HDs between the section 430C and the sections 410A, 410B and 410D are 2. Furthermore, the Inter-HD between the sections SEC_3 (e.g., 430C and 410C) having the same location under the different operating conditions is not available (NA). Furthermore, the Inter-HD counter 250 of FIG. 2 is capable of finding the largest value and the least value among the Inter-HDs between the sections SEC_1 through SEC_4 under the first operating condition Cond_1 and the third operating condition Cond_3, so as to obtain the maximum Inter-HD MAX_HD and the minimum Inter-HD MIN_HD of the memory array 120A.

FIG. 6D shows the table illustrating the Inter-HDs of the contents between the sections 410A through 410C of FIG. 4A and the section 430D of FIG. 4C. Similarly, the content "0110" of the section 430D are different from the content "0101" of the sections 410A through 410C, the intermediate results XOR_SECTION determined by the Hamming magnitude comparator 240 are "0011", and the Inter-HDs are 2 in FIG. 6D.

In some embodiments, the Inter-HD counter 250 records the whole Inter-HDs between the sections SEC_1 through SEC_4 under the different operating conditions, and finds the largest value and the least value among the recorded whole Inter-HDs. For example, the Inter-HD counter 250 stores the 12 Inter-HDs of FIGS. 5A through 5D and the 12 Inter-HDs of FIGS. 6A through 6D into a storage device, and then finds the largest value and the least value among the 24 Inter-HDs. Thus, the Inter-HD counter 250 determines that the maximum Inter-HD MAX_HD is "3" and the minimum Inter-HD MIN_HD is "0".

In some embodiments, the Inter-HD counter 250 updates the maximum Inter-HD MAX_HD and the minimum Inter-HD MIN_HD according to the result of each bitwise XOR operation. For example, according to the Inter-HDs of FIGS. 5A through 5D, the Inter-HD counter 250 assigns "1" as the maximum Inter-HD MAX_HD and "0" as the minimum Inter-HD MIN_HD for the memory array 120A. Next, after obtaining the Inter-HDs of FIGS. 6A through 6D, the Inter-HD counter 250 updates the maximum Inter-HD MAX_HD to "3". Specifically, if the Inter-HD determined by the Hamming magnitude comparator 240 is greater than the current maximum Inter-HD MAX_HD, the Inter-HD counter 250 assigns the Inter-HD as the maximum Inter-HD MAX_HD. If the Inter-HD determined by the Hamming magnitude comparator 240 is less than the current minimum Inter-HD MIN_HD, the Inter-HD counter 250 assigns the Inter-HD as the minimum Inter-HD MIN_HD. According to "3" of the maximum Inter-HD MAX_HD and "0" of the minimum Inter-HD MIN_HD in FIGS. 5A-5D and 6A-6D, the Inter-HD range of the memory array 120A is (0/4, 3/4). Converted into percentage, the Inter-HD range of the memory array 120A is (0%, 75%). As described above, according to the Inter-HD range and Intra-HD range of the memory array, it is determined whether the PUFs are sufficient for the security feature of the memory array 120A. In some embodiments, the Intra-HD range of the memory array 120A is obtained in advance.

Figure 7:
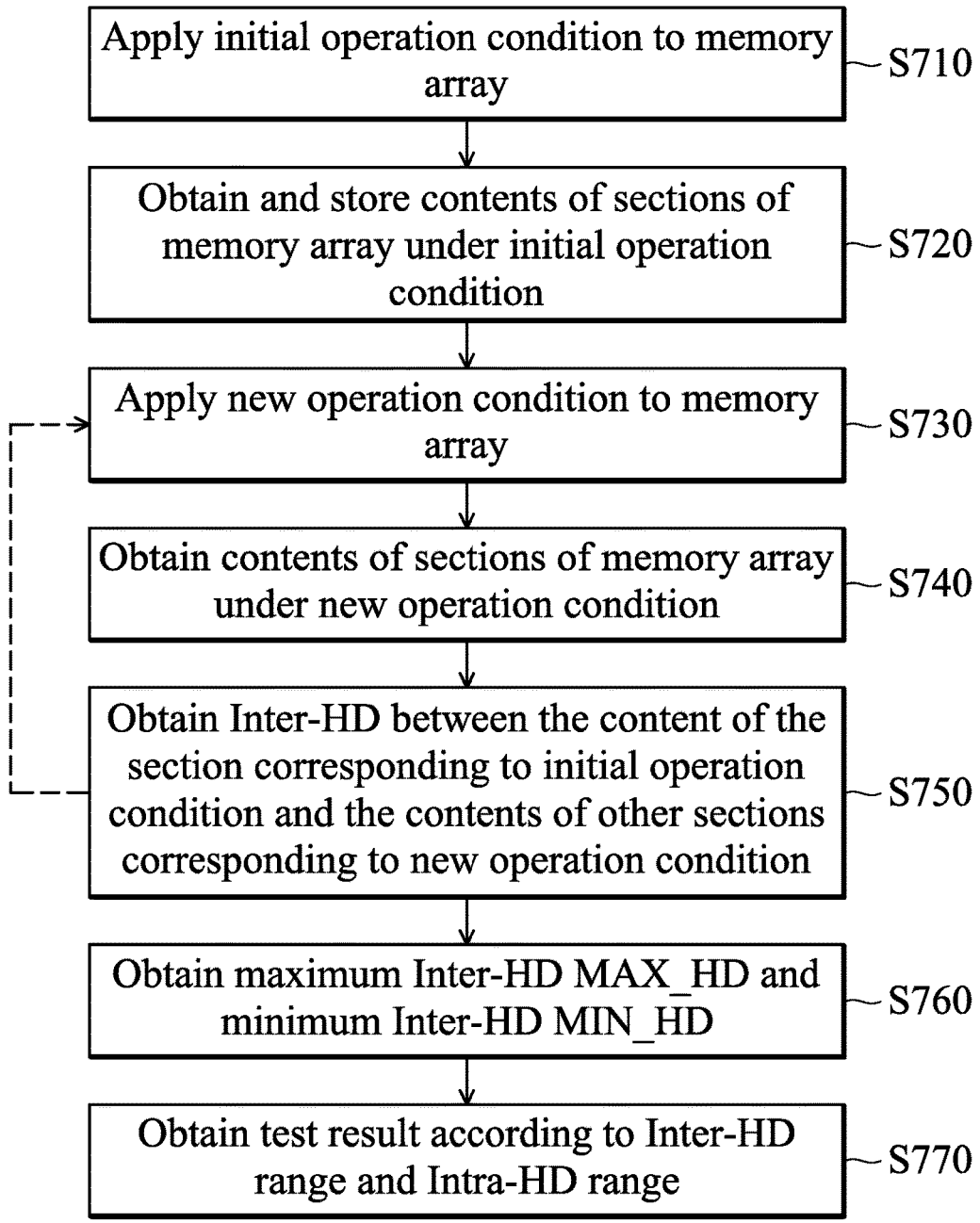
FIG. 7 shows a test method for testing a memory array, in accordance with some embodiments of the disclosure.

FIG. 7 shows a test method for testing a memory array 120 of FIG. 1, in accordance with some embodiments of the disclosure. The memory array 120 is formed by multiple memory cells, and the memory cells are divided into multiple sections SEC_1 through SEC_n. Each of the sections SEC_1 through SEC_n has its individual location in the memory array. In some embodiments, the method of FIG. 7 is performed using a test apparatus or a test machine for verifying a wafer or a device including one or more memory arrays.

In operation S710, the test apparatus applies an initial operating condition (e.g., the first operating condition Cond_1) to the memory array. In the initial operating condition, the power supply PWR with an initial voltage level, the operation clock CLK with an initial frequency value, and/or an operation temperature with an initial temperature value are applied to the memory array 120 through the test apparatus.

In operation S720, when the memory array 120 is operating under the initial operating condition, the test apparatus access the memory array 120 through the related signals (e.g., the command signal CMD and the address signal ADDR of FIG. 1), so as to read out the contents of the sections SEC_1 through SEC_n of the memory array 120 regarding the response of the PUF under the initial operating condition. In some embodiments, the response of the PUF under the initial operating condition is obtained based on the power-up states of the memory cells in the memory array. Furthermore, the test apparatus stores the contents of the sections SEC_1 through SEC_n of the memory array 120 as initial contents for measuring the Inter-HDs of the memory array. In some embodiments, the contents of the sections SEC_1 through SEC_n of the memory array 120 represent the response of the PUF obtained from speed comparison of memory cells corresponding to the operation clock CLK or from an initialized state of the memory cells corresponding to the power supply PWR in the memory array 120.

In operation S730, the test apparatus applies a new operating condition (e.g., the second operating condition Cond_2) to the memory array. In some embodiments, the voltage level of the power supply PWR, the frequency value, duty cycle or slew rate of the operation clock CLK, or the temperature value of the operation temperature may be different from that of the initial operating condition. For example, in the new operating condition, the power supply PWR with a voltage level different from the initial voltage level, the operation clock CLK with a frequency value different from the initial frequency value, and/or an operation temperature with a temperature value different from the initial temperature value are applied to the memory array 120 through the test apparatus.

In operation S740, when the memory array 120 is operating under the new operating condition, the test apparatus access the memory array 120 through the related signals again, so as to read out the contents of the sections SEC_1 through SEC_n of the memory array 120 regarding the response of the PUF under the new operating condition. In some embodiments, the characteristics of the power supply PWR, the operation clock CLK and the operation temperature of the new operating condition are different from that of the initial operating condition, and the response of the PUF under the new operating condition is different from the response of the PUF under the initial operating condition.

In operation S750, the Inter-HDs between the content of the section under the initial operating condition and the contents of other sections under the new operating condition are obtained. In some embodiments, the Inter-HDs are determined by the hamming magnitude comparator 240 of FIG. 2. Furthermore, no Inter-HD between the content of the section under the initial operating condition and the content of the same section under the new operating condition is obtained. As described above, if the number of sections of the memory array 120 is N, the number of Inter-HDs obtained in operation S750 is N×(N−1).

In some embodiments, the operations S730 through S750 can be repeated until all of the operating conditions have been applied to the memory array.

In operation S760, a maximum Inter-HD MAX_HD and a minimum Inter-HD MIN_HD of the memory array 120 among the whole Inter-HDs are obtained. Thus, an Inter-HD range of the memory array 120 is obtained according to the maximum Inter-HD MAX_HD and the minimum Inter-HD MIN_HD.

As described above, the method of FIG. 7 is performed by using a test apparatus or a test machine for verifying a wafer or a device including one or more memory arrays. According to the operations 750 and 760, the test apparatus or the test machine is capable of obtaining the maximum Inter-HD MAX_HD, the minimum Inter-HD MIN_HD and the Inter-HD range of the one or more memory arrays in an on-line (or in-line) manner without loading the contents of all of the responses in an off-line manner, thereby speeding up test time for the one or more memory arrays.

In operation S770, according to the Inter-HD range of the memory array 120 obtained in operation S760 and the known Intra-HD range of the memory array, a test result of the memory array 120 is obtained. As described above, if the Inter-HD range does not overlay the Intra-HD range, the test result indicates that verification of the memory array 120 is successful and PUFs of the memory array 120 are hard to predict. Conversely, if the Inter-HD range overlays the Intra-HD range, the test result indicates that verification of the memory array 120 is unsuccessful and PUFs of the memory array 120 are easy to predict.

Embodiments for an inter-hamming distance analyzer and methods for testing and measuring inter-hamming distance of a memory array are provided. The inter-hamming distance analyzer and the memory array are implemented in a memory device. By using the inter-hamming distance analyzer to verify Intra-HD and Inter-HD of manufactured PUFs of the memory array under various operating conditions without downloading whole bits generated with PUFs from the memory array. Therefore, time consuming and the storage spaces for storing the bits from all dies or wafers operating at all different conditions (such as supply voltage, temperature, and frequency etc.) are decreased.

In some embodiments, a memory device is provided, wherein the memory device includes a memory array including a plurality of sections, and an inter-hamming difference analyzer. Each section includes a plurality of bits, and the numbers of the bits of the plurality of sections are the same. The inter-hamming difference analyzer is configured to obtain contents of the plurality of sections operating in different operating conditions, to obtain a plurality of inter-hamming differences of the contents, and to provide a maximum inter-hamming difference and a minimum inter-hamming difference among the inter-hamming differences of the plurality of sections. The inter-hamming difference represents the number of unlike bits between the content of one section of the plurality of sections corresponding to a first operating condition and the content of another section of the plurality of sections corresponding to a second operating condition that is different from the first operating condition.

In some embodiments, a method for measuring inter-hamming difference of a memory array divided into a plurality of sections is provided. A plurality of first contents of the plurality of sections are obtained from the memory array when the memory is operating in a first operating condition. A plurality of second contents of the plurality of sections are obtained from the memory array when the memory is operating in a second operating condition. Power supplies, operation frequencies or operation temperatures of the first and second operating conditions are different. A plurality of inter-hamming differences between the first and second contents are obtained. The inter-hamming difference represents the number of unlike bits between the first content of one section of the plurality of sections and the second content of another section of the plurality of sections. An inter-hamming difference range is obtained according to a maximum inter-hamming difference and a minimum inter-hamming difference among the inter-hamming differences.

In some embodiments, a method for testing a memory array divided into a plurality of sections is obtained. A first operating condition is applied to the memory array, and obtaining a plurality of first contents of the plurality of sections from the memory array operating in the first operating condition. After storing the first contents, a second operating condition is applied to the memory device, and a plurality of second contents of the plurality of sections are obtained from the memory array operating in the second operating condition. A plurality of inter-hamming differences between the stored first contents and the second contents are obtained. The inter-hamming difference represents the number of unlike bits between the recorded first content of one section of the plurality of sections and the second content of another section of the plurality of sections. A test result of the memory device is obtained according to a maximum inter-hamming difference and a minimum inter-hamming difference among the inter-hamming differences.

The foregoing outlines nodes of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A memory device, comprising:
a memory array comprising a plurality of sections, wherein each section of the plurality of sections comprises a plurality of bits, and the numbers of the bits of the plurality of sections are the same; and
an inter-hamming difference analyzer configured to obtain contents of the plurality of sections operating in different operating conditions, to obtain a plurality of inter-hamming differences of the contents, and to provide a maximum inter-hamming difference and a minimum inter-hamming difference among the inter-hamming differences of the plurality of sections,
wherein the inter-hamming difference represents the number of unlike bits between the content of one section of the plurality of sections corresponding to a first operating condition and the content of another section of the plurality of sections corresponding to a second operating condition that is different from the first operating condition.

2. The memory device as claimed in claim 1, wherein the inter-hamming difference analyzer comprises:
a storage device configured to store the contents of the plurality of sections corresponding to the first operating condition; and a comparator configured to determine the hamming differences between the content of a first section of the plurality of sections corresponding to the second operating condition and the contents of a plurality of sections other than the first section stored in the storage device.

3. The memory device as claimed in claim 2, wherein the storage device has the same capacity as the memory array.

4. The memory device as claimed in claim 3, wherein when the inter-hamming difference analyzer obtains a first content of the first section from the memory array operating in the second operating condition, the comparator determines the inter-hamming differences between the first content of the first section from the memory array and the contents of the plurality of sections except the first section from the storage device, wherein the number of inter-hamming differences is equal to the number of sections of the memory array minus one.

5. The memory device as claimed in claim 1, wherein the section of the memory array has an individual location in the memory array, and the inter-hamming difference analyzer determines the inter-hamming difference between a first content of a first section of the plurality of sections corresponding to the first operating condition and a second content of a second section of the plurality of sections corresponding to the second operating condition, wherein the first section and the second section have different locations in the memory array.

6. The memory device as claimed in claim 5, wherein when the determined inter-hamming difference is greater than the maximum inter-hamming difference, the inter-hamming difference analyzer assigns the determined inter-hamming difference as the maximum inter-hamming difference, and when the determined inter-hamming difference is less than the minimum inter-hamming difference, the inter-hamming difference analyzer assigns the determined inter-hamming difference as the minimum inter-hamming difference.

7. The memory device as claimed in claim 1, wherein power supplies, operation frequencies or operation temperatures of the first and second operating conditions are different.

8. The memory device as claimed in claim 1, wherein when the number of sections of the memory array is N, and the number of inter-hamming differences of the contents of the plurality of sections between the first and second operating conditions is N×(N−1).

9. A method for measuring inter-hamming difference of a memory array divided into a plurality of sections, comprising:
obtaining a plurality of first contents of the plurality of sections from the memory array when the memory array is operating in a first operating condition;
obtaining a plurality of second contents of the plurality of sections from the memory array when the memory array is operating in a second operating condition, wherein power supplies, operation frequencies or operation temperatures of the first and second operating conditions are different;
obtaining a plurality of inter-hamming differences between the first and second contents, wherein the inter-hamming difference represents the number of unlike bits between the first content of one section of the plurality of sections and the second content of another section of the plurality of sections; and obtaining an inter-hamming difference range according to a maximum inter-hamming difference and a minimum inter-hamming difference among the inter-hamming differences.

10. The method as claimed in claim 9, further comprising:
obtaining a test result of the memory array according to the inter-hamming difference range and an intra-hamming difference range.

11. The method as claimed in claim 9, further comprising:
storing the first contents of the plurality of sections from the memory array into a storage device having the same capacity as the memory array.

12. The method as claimed in claim 9, wherein obtaining the inter-hamming differences between the first and second contents further comprises:
according to the first content of a first section of the plurality of sections corresponding to the first operating condition, determining the inter-hamming differences between the first content of the first section and the second contents of the plurality of sections except for the first section corresponding to the second operating condition,
wherein the number of inter-hamming differences corresponding to the first content is equal to the number of sections of the memory array minus one.

13. The method as claimed in claim 9, wherein the section has an individual location in the memory array, and obtaining the inter-hamming differences between the first and second contents further comprises:
determining the inter-hamming difference between the first content of a first section of the plurality of sections corresponding to the first operating condition and the second content of a second section of the plurality of sections corresponding to the second operating condition,
wherein the first section and the second section have different locations in the memory array.

14. The method as claimed in claim 13, further comprising:
assigning the determined inter-hamming difference as the maximum inter-hamming difference when the determined inter-hamming difference is greater than the maximum inter-hamming difference; and
assigning the determined inter-hamming difference as the minimum inter-hamming difference when the determined inter-hamming difference is less than the minimum inter-hamming difference.

15. The method as claimed in claim 9, wherein when the number of sections of the memory array is N, and the number of inter-hamming differences of the contents of the plurality of sections between the first and second operating conditions is N×(N−1).

16. A method for testing a memory array divided into a plurality of sections, comprising:
applying a first operating condition to the memory array, and obtaining a plurality of first contents of the plurality of sections from the memory array operating in the first operating condition;
after storing the first contents, applying a second operating condition to the memory array, and obtaining a plurality of second contents of the plurality of sections from the memory array operating in the second operating condition;
obtaining a plurality of inter-hamming differences between the stored first contents and the second contents, wherein the inter-hamming difference represents the number of unlike bits between the stored first content of one section of the plurality of sections and the second content of another section of the plurality of sections; and obtaining a test result of the memory array according to a maximum inter-hamming difference and a minimum inter-hamming difference among the inter-hamming differences.

17. The method as claimed in claim 16, wherein obtaining the inter-hamming differences between the stored first contents and the second contents further comprises:

according to the stored first content of a first section corresponding to the first operating condition, determining the inter-hamming differences between the stored first content of the first section and the second contents of the plurality of sections except for the first section corresponding to the second operating condition, wherein the number of inter-hamming differences corresponding to the first content is equal to the number of sections of the memory array minus one.

18. The method as claimed in claim 16, wherein the section has an individual location in the memory array, and obtaining the inter-hamming differences between the stored first contents and the second contents further comprises:

determining the inter-hamming difference between the stored first content of a first section corresponding to the first operating condition and the second content of a second section corresponding to the second operating condition, wherein the first section and the second section have different locations in the memory array.

19. The method as claimed in claim 18, further comprising:

assigning the determined inter-hamming difference as the maximum inter-hamming difference when the determined inter-hamming difference is greater than the maximum inter-hamming difference; and assigning the determined inter-hamming difference as the minimum inter-hamming difference when the determined inter-hamming difference is less than the minimum inter-hamming difference.

20. The method as claimed in claim 16, wherein when the number of sections of the memory array is N, and the number of inter-hamming differences of the contents of the plurality of sections between the first and second operating conditions is N×(N−1).

* * * * *